United States Patent [19]

Eilingsfeld et al.

[11] Patent Number: 4,533,612
[45] Date of Patent: Aug. 6, 1985

[54] ELECTROPHOTOGRAPHIC RECORDING MATERIALS CONTAINING SPECIAL CHARGE CARRIER-TRANSPORTING COMPOUNDS

[75] Inventors: Heinz Eilingsfeld; Karl-Heinz Etzbach, both of Frankenthal; Gerhard Hoffmann, Otterstadt; Peter Neumann, Wiesloch, all of Fed. Rep. of Germany

[73] Assignee: BASF Aktiengesellschaft, Fed. Rep. of Germany

[21] Appl. No.: 675,264

[22] Filed: Nov. 27, 1984

Related U.S. Application Data

[63] Continuation of Ser. No. 489,186, Apr. 27, 1983, abandoned.

[51] Int. Cl.$^3$ ............ G03G 5/06; G03G 5/14
[52] U.S. Cl. ............ 430/59; 430/76; 430/49
[58] Field of Search ............ 430/57, 58, 59, 60, 430/76

[56] References Cited

U.S. PATENT DOCUMENTS 4,232,103 11/1980 Limberg ............ 430/58
4,418,133 11/1983 Katagiri ............ 430/58

FOREIGN PATENT DOCUMENTS 1058836 6/1959 Fed. Rep. of Germany .
1120875 12/1961 Fed. Rep. of Germany .
1117391 5/1962 Fed. Rep. of Germany .
1522497 2/1970 Fed. Rep. of Germany .
2220408 4/1972 Fed. Rep. of Germany .

*Primary Examiner*—John L. Goodrow
*Attorney, Agent, or Firm*—Keil & Weinkauf

[57] ABSTRACT

Electrophotographic recording materials which comprise an electrically conductive base, charge carrier-producing compounds (sensitizers), and charge carrier-transporting compounds, possess high photoconductivity and low conductivity in the dark, and contain, as charge carrier-transporting compounds, 2-substituted benzotriazoles of the formula

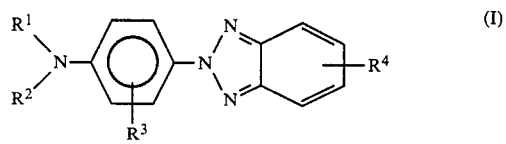

are used for reprographic purposes and for the production of electrophotographic printing plates, in particular offset printing plates.

14 Claims, No Drawings

ELECTROPHOTOGRAPHIC RECORDING MATERIALS CONTAINING SPECIAL CHARGE CARRIER-TRANSPORTING COMPOUNDS

This application is a continuation of application Ser. No. 489,186, filed on Apr. 27, 1983, now abandoned.

The present invention relates to electrophotographic recording materials which comprise an electrically conductive base, charge carrier-producing compounds, and special charge carrier-transporting compounds.

Electrophotographic processes, materials required for these, and a variety of different structures for recording materials have been disclosed. Advantageous materials for use in the reprography sector are those comprising a polymeric binder which can be adapted to the special requirements of the particular field of use, low molecular weight organic compounds which are soluble, even in relatively high concentrations, in the binder and are capable of transporting charge carriers, and compounds, in particular dyes or pigments, which produce charge carriers when exposed imagewise to actinic light, and are capable of transferring these charge carriers to the charge-transporting compounds, with the aid of the electric field exerted from outside by the electrostatic surface charge. Depending on the field of use of the recording material, these charge carrier-producing compounds can be incorporated, as a separate layer, in a composite structure (cf. German Laid-Open Application DOS 2,220,408), or may be present in the form of a monodisperse solution of the dye molecules in a mixture of the binder and the charge carrier-transporting compounds (cf. German Pat. No. 1,058,836). The multi-layer electrophotographic recording material described in German Laid-Open Application DOS 2,220,408 comprises an electrically conductive base, a first layer which is about 0.005-2 μm thick, contains a dye and produces charge carriers when exposed to actinic light, and a second layer which is composed of organic materials which are insulating in the dark and contain one or more charge-transporting compounds.

It has also been disclosed that photosemiconducting organic compounds may be used for the production of electrophotographic printing plates, in particular electrophotographic offset printing plates (cf. German Pat. Nos. 1,117,391 and 1,120,875 and German Published Applications DAS 1,522,497 and DAS 2,726,116).

The increased demands on reprographic systems necessitate a large variety of recording materials and systems in order that special problems can be solved in an optimum manner. The characteristics desired include high photosensitivity, good resolution and good toning properties. Poor toning, which is frequently objected to and which indicates inadequate differentiation between the field strengths of the exposed and nonexposed areas, is often attributable to the fact that the recording material in the charged state possesses an excessively high conductivity in the dark, so that there is an inadequate surface charge density before imagewise exposure to actinic light.

It is an object of the present invention to provide further electrophotographic recording materials which are suitable, in particular, for the production of electrophotographic printing plates, such as offset printing plates, and which are highly photosensitive and exhibit good resolution and processability and low conductivity in the dark.

We have found that this object is achieved, and that electrophotographic recording materials which comprise an electrically conductive base, charge carrier-producing compounds and charge carrier-transporting compounds and which exhibit the above properties are obtained, if the recording materials contain, as charge carrier-transporting compounds, those of the formula (I)

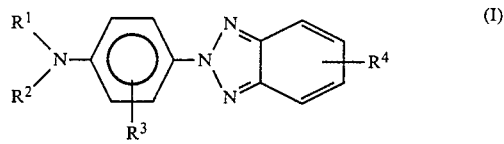

where $R^1$ and $R^2$ are identical or different and are each hydrogen, alkyl, allyl, benzyl or unsubstituted or substituted phenyl, or $R^1$ and $R^2$ together are

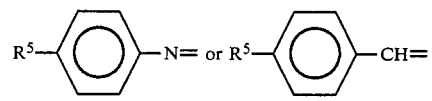

where $R^5$ is $NR^1R^2$, $R^3$ is hydrogen, alkyl, alkoxy or halogen and $R^4$ is hydrogen, alkyl, alkoxy, vinyl, allyl, dialkylamino, nitro, cyano or acryloyl.

Preferred compounds of this type are those of the formula (I) where $R^1$ is hydrogen, alkyl, benzyl or phenyl, $R^2$ is alkyl, benzyl or phenyl, $R^3$ is hydrogen and $R^4$ is hydrogen, alkoxy or halogen. $R^4$ is preferably in the 6-position of the 1,2,3-benzotriazole.

Examples of very suitable compounds are (1) 2-(4'-diethylaminophenyl)-1,2,3-benzotriazole

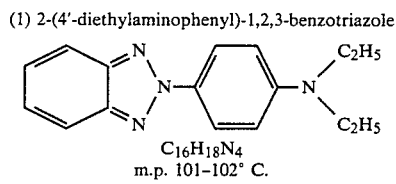

$C_{16}H_{18}N_4$
m.p. 101–102° C.

(2) 2-(4'-diethylaminophenyl)-6-methoxy-1,2,3-benzotriazole

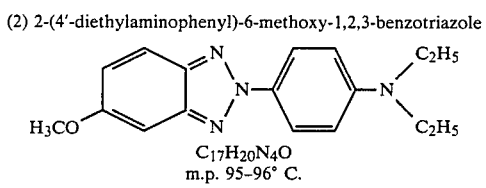

$C_{17}H_{20}N_4O$
m.p. 95–96° C.

(3) 2-(4'-diethylaminophenyl)-6-chloro-1,2,3-benzotriazole

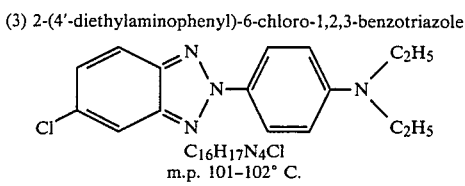

$C_{16}H_{17}N_4Cl$
m.p. 101–102° C.

(4) 2-(4'-ethylbenzylaminophenyl)-1,2,3-benzotriazole

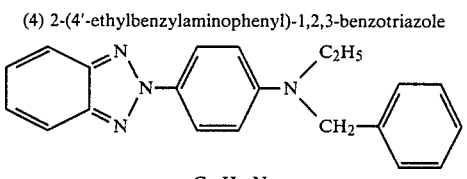

$C_{21}H_{20}N_4$
m.p. 120–122° C.

(5) 2-(4'-ethylbenzylaminophenyl)-6-methoxy-1,2,3-benzotriazole

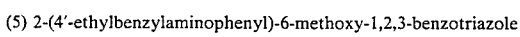

-continued

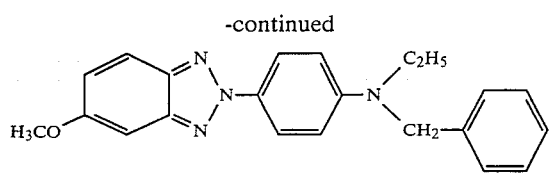

C22H22N4O
m.p. 105–106° C.

(6) 2-(2'-Methyl-4'-diethylaminophenyl)-1,2,3-benzotriazole

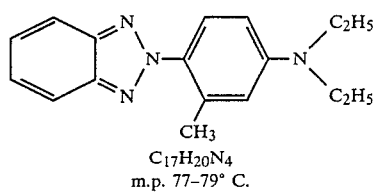

C17H20N4
m.p. 77–79° C.

(7) 2-(4'-dibenzylaminophenyl)-6-methoxy-1,2,3-benzotriazole

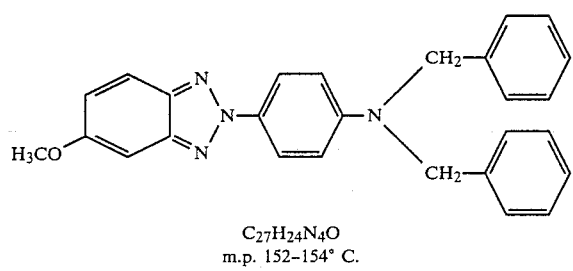

C27H24N4O
m.p. 152–154° C.

(8) 2-(4'-diethylaminophenyl)-6-methyl-1,2,3-benzotriazole

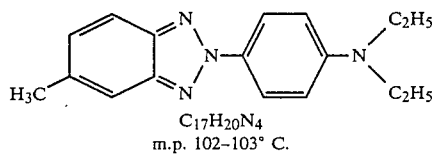

C17H20N4
m.p. 102–103° C.

(9) 2-(4'-methylphenylaminophenyl)-1,2,3-benzotriazole

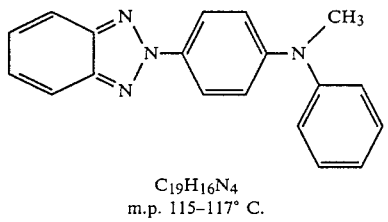

C19H16N4
m.p. 115–117° C.

(10) 2-(4'-diethylaminophenyl)-6-ethoxy-1,2,3-benzotriazole

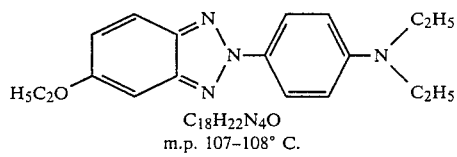

C18H22N4O
m.p. 107–108° C.

(11) 2-(4'-diethylaminophenyl)-6-benzyloxy-1,2,3-benzotriazole

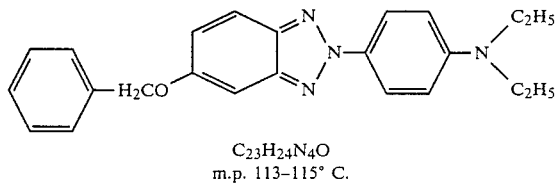

C23H24N4O
m.p. 113–115° C.

(12) 2-(4'-methylphenylaminophenyl)-6-methoxy-1,2,3-benzotriazole

-continued

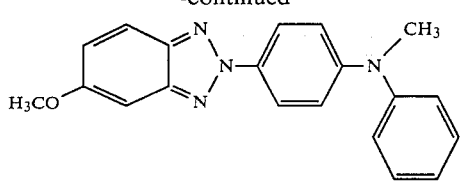

C20H18N4O
m.p. 109–110° C.

(13) 2-(4'-ethylbenzylaminophenyl)-6-ethoxy-1,2,3-benzotriazole

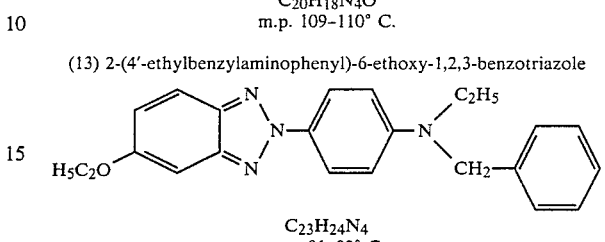

C23H24N4
m.p. 91–92° C.

(14) 2-(4'-diethylaminophenyl)-6-diethylamino-1,2,3-benzotriazole

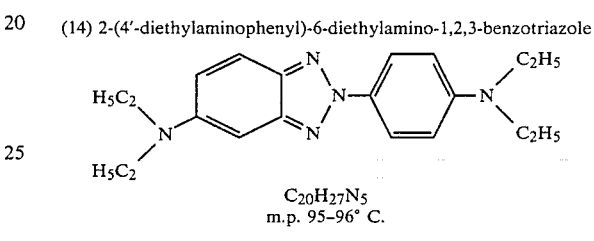

C20H27N5
m.p. 95–96° C.

(15) 2-(4'-diethylaminophenyl)-6-1,2,3-fluorobenzotriazole

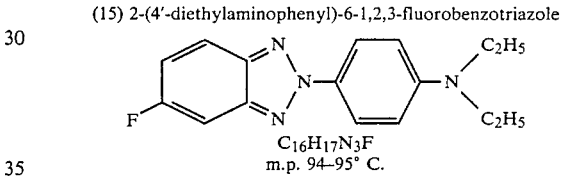

C16H17N3F
m.p. 94–95° C.

The substituted phenylbenzotriazoles used according to the invention can be prepared by conventional methods used in organic chemistry.

They can for example be obtained from orthoaminoazo compounds of the formula (II)

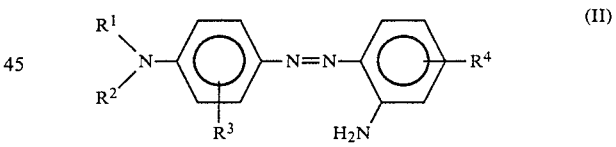

or from ortho-nitroazo compounds of the formula (III)

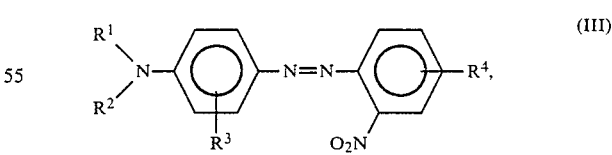

where $R^1$, $R^2$, $R^3$ and $R^4$ have the above meanings, using the methods described by Houben-Weyl in Methoden der organischen Chemie, 4th Edition, Vol. X/3, pages 425 et seq. The compounds of the formulae (II) and (III) are known and can be prepared by conventional processes.

The compounds which transport charge carriers when exposed to light, and which are used in accordance with the invention, can be employed with advantage in both single-layer and multi-layer recording systems on an electrically conductive base.

Suitable single-layer systems have, preferably on a conductive base, a layer of (a) from 45 to 75 parts by weight of a binder, (b) from 30 to 60, in particular from 35 to 50, parts by weight of one of the charge carrier-transporting compounds used according to the invention, (c) if appropriate from 5 to 25 parts by weight of another, essentially inactive binder and (d) from 0.05 to 0.8 part by weight of a compound which produces charge carriers when exposed to actinic light, in particular a suitable dye. Advantageously, an about 5% strength by weight solution in a suitable organic solvent is applied to the clean conductive base so as to give a layer which is about 0.8–40 μm thick after the solvent has been evaporated off in the air. The thickness of the layer depends on the intended use, and is, in particular, from 0.8 to 6 μm in the case of electrophotographic printing plates.

Suitable multi-layer systems possess, on an electrically conductive base, for example (a) a charge carrier-producing layer and (b) a charge-transporting layer comprising (b1) from 30 to 60 parts by weight of one or more charge carrier-transporting compounds of the formula (I), and (b2) from 45 to 75 parts by weight of an organic binder, with or without (b3) from 5 to 25 parts by weight of further additives which improve the mechanical properties of the layer. The first layer is advantageously applied to the base in a thickness of from 0.005 to 5, in particular from 0.1 to 0.9, μm, from solution in a suitable solvent. After this layer has been applied, the second layer is applied so that a layer of from 5 to 25, in particular from 7 to 15, μm thick results after the composite structure has been dried.

In principle, any electrically conductive base can be employed, provided that it is suitable for the field of use of the recording material. Depending on the field of use, preferred bases are aluminum, zinc, magnesium, copper or multimetal sheets, for example crude or pretreated, eg. roughened and/or anodized, aluminum sheets, aluminum foils, polymer films with metallized surfaces, such as polyethylene terephthalate films coated with aluminum by vapor deposition, and special electrically conductive papers. Bases for printing plates are advantageously from 0.08 to about 0.3 mm thick.

The use for which the recording material is intended determines which type of organic binder is suitable for the layers. Examples of suitable binders for the copying sector are cellulose ethers, polyester resins, polyvinyl chlorides, polycarbonates, copolymers, eg. styrene/-maleic anhydride or vinyl chloride/maleic anhydride copolymers, or mixtures of these. The choice of binders is governed in particular by their film-forming and electrical properties, their adhesion to the base and their solubility properties. Particularly suitable recording materials for the production of electrophotographic printing plates, especially offset printing plates, are those which are soluble in basic aqueous or alcoholic solvents. These are, in particular, substances possessing groups which make them soluble in alkali, eg. anhydride, carboxyl, sulfonic acid, phenol or sulfonimide groups. Preferred binders are those which in particular have a high acid number, and are readily soluble in basic aqueous-alcoholic solvent systems and have a mean weight average molecular weight of from 800 to 50,000, in particular from 1,500 to 10,000. Examples of suitable binders are copolymers of methacrylic acid and methacrylates, in particular those of styrene with maleic anhydride and of styrene, methacrylic acid and methacrylates, provided that they possess the above solubility properties. Although it is known that binders possessing free carboxyl groups cause an undesirable increase in the conductivity of electrophotographic layers in the dark and hence result in poor toning, such binders can be readily made compatible with the benzotriazoles used in accordance with the invention. Thus, we have found that styrene/maleic anhydride/acrylic or methacrylic acid copolymers which contain from 5 to 50% by weight of maleic anhydride as copolymerized units and from 5 to 35, in particular from 10 to 30, % by weight of acrylic or methacrylic acid as copolymerized units give satisfactory electrophotographic layers having adequate conductivity in the dark. They are highly soluble in washout solutions containing 75% by weight of water, 23% by weight of isobutanol and 2% by weight of sodium carbonate, but are insoluble in fountain solutions conventionally used for offset plates.

Examples of suitable charge carrier-producing compounds or sensitizers for single-layer systems, as also used for the production of electrophotographic printing plates, are triarylmethane dyes, xanthene dyes and cyanine dyes. Very good results were obtained when the compounds according to the invention, of the formula I, were used together with rhodamine B (C.I. 45170), rhodamine 6 G (C.I. 45160), malachite green (C.I. Basic Green 4, C.I. 42000), methyl violet (C.I. 42535) or crystal violet (C.I. 42555). In multi-layer systems, the dye or the pigment is present in a separate charge carrier-producing layer. In this case, azo dyes, phthalocyanines, isoindoline dyes and perylenetetracarboxylic acid derivatives are particularly effective. Good results are achieved with perylene-3,4:9,10-tetracarboxylic acid diimide derivatives, as described in German Laid-Open Applications DOS 3,110,954 and DOS 3,110,960.

Depending on the use to which it is put, the electrophotographic recording material according to the invention can contain conventional additives, for example flow improvers and plasticizers in the photoconductive layer, or adhesive layers between the base and the layer.

The novel electrophotographic recording materials have a combination of very good properties, in particular high photoconductivity coupled with very low conductivity in the dark, and are hence very useful for the copying sector.

They possess substantial advantages when used for the production of electrophotographic printing plates, satisfying high requirements in respect of resolution and print run. When the plate is processed in a reproduction camera, the high photosensitivity permits the exposure time to be reduced by up to about half compared with conventional materials. The very crisp image reproduction results in good resolution, and, as a result of high charge contrast, it is also possible to obtain good reproduction of fine halftone dots in highlight areas. Furthermore, exposure of the layers results in very low residual potentials, and the images obtained during toning are free from ground in the non-image areas. The spectral sensitivity decreases sharply at 600 nm, so that the layers can be handled in red light, without image loss occurring.

Electrophotographic offset printing plates are produced in a conventional manner by charging the electrophotographic recording material electrostatically by means of a high-voltage corona, following this directly by imagewise exposure, developing the resulting latent electrostatic charge image by means of a dry or liquid toner, fixing the toner in a downstream melting process and removing the non-toned photosemiconducting layer by means of a suitable washout solvent. The resulting printing plate can then be prepared in a conventional manner for offset printing, this preparation comprising, for example, hydrophilizing and gumming the water-bearing surface.

Although it was known that heterocyclic derivatives, such as oxadiazole derivatives (cf. German Pat. No. 1,058,836), oxazole derivatives (cf. German Pat. No. 1,120,875) or 2,5-bis-(4'-dialkylaminophenyl)-1,3,4-triazoles (cf. German Published Application DAS 1,060,260), could be used as charge carrier-transporting compounds, the combination of advantageous properties achieved with the aminophenylbenzotriazoles used according to the invention certainly could not be foreseen. Although German Laid-Open Application DOS 2,737,334 describes the use of benzotriazole, together with a binder, a reducible metal compound and a reducing agent for this compound, in an electrically conductive mass for an image-recording element which can be developed by heat, this publication does not suggest the results of the present invention.

The Examples which follow illustrate the invention, parts and percentages being by weight.

The measured Xerographic values A to G given in the Examples were determined as follows:

The layers were charged uniformly to a surface potential of 600 volts by means of a corona at a direct current voltage of $-7.5$ kv at a distance of 1 cm, and were then exposed to white light from a xenon lamp with a luminous intensity of about 0.85 mw.cm$^{-2}$. The following measurements were carried out:

A: Time, in milliseconds (ms), during which the surface potential present before exposure falls to half its value (300 V) on exposure to actinic light.

B: Decrease in potential, in volt (V), which occurs in the same time in the dark as the result of the conductivity of the layers.

C: Surface potential, in volt (V), reached after a charging time of 20 seconds.

D: Decrease in potential in %, based on measured value C, which occurs in the dark in the course of 20 seconds.

E: Decrease in potential as a result of exposure to actinic light, in %, based on the initial potential directly before exposure.

F: Change in potential per second at the beginning of exposure (V/s) in the case of an initial potential of 1000 volts.

G: Difference in potential in volt (V) between exposed and non-exposed areas of the charged layers.

Benzotriazoles used:
(1) 2-(4'-diethylaminophenyl)-1,2,3-benzotriazole,
(2) 2-(4'-diethylaminophenyl)-6-methoxy-1,2,3-benzotriazole,
(3) 2-(4'-diethylaminophenyl)-6-chloro-1,2,3-benzotriazole,
(4) 2-(4'-ethylbenzylaminophenyl)-1,2,3-benzotriazole,
(5) 2-(4'-ethylbenzylaminophenyl)-6-methoxy-1,2,3-benzotriazole,
(6) 2-(2'-Methyl-4'-diethylaminophenyl)-1,2,3-benzotriazole,
(7) 2-(4'-dibenzylaminophenyl)-6-methoxy-1,2,3-benzotriazole,
(8) 2-(4'-diethylaminophenyl)-6-methyl-1,2,3-benzotriazole,
(9) 2-(4'-methylphenylaminophenyl)-1,2,3-benzotriazole,
(10) 2-(4'-diethylaminophenyl)-6-ethoxy-1,2,3-benzotriazole,
(11) 2-(4'-diethylaminophenyl)-6-benzyloxy-1,2,3-benzotriazole,
(12) 2-(4'-methylphenylaminophenyl)-6-methoxy-1,2,3-benzotriazole,
(13) 2-(4'-ethylbenzylaminophenyl)-6-ethoxy-1,2,3-benzotriazole,
(14) 2-(4'-diethylaminophenyl)-6-diethylamino-1,2,3-benzotriazole,
(15) 2-(4'-diethylaminophenyl)-6-1,2,3-fluorobenzotriazole.

EXAMPLES 1 TO 6

A layer comprising 60 parts of a chlorinated perylene-3,4:9,10-tetracarboxylic acid diimide bis-benzimidazole with a chlorine content of about 38% and 50 parts of a copolymer of vinyl chloride, acrylic acid and a maleic acid diester was applied, as a charge carrier-producing layer, in a thickness of about 0.55 µm, to a polyethylene terephthalate film provided, by vapor deposition, with a conductive aluminum layer of about 300 Å thickness.

A charge-transporting layer comprising 55 parts of a commercial polycarbonate binder having a melting range of from 220° to 230° C. and 40 parts of one of the benzotriazoles listed above under (1) to (15) was applied, from a solution in ethyl acetate, to the above charge carrier-producing layer, the solvent was evaporated off in the air and drying was carried out for 30 minutes at 80° C., the resulting dry layer being 12 µm thick.

TABLE 1

Measured xerographic values for the recording materials of Examples 1 to 6.

| Example | Benzotriazole | A (ms) | B (V) | C (V) |
|---|---|---|---|---|
| 1 | (1) | 190 | 0.25 | 2,900 |
| 2 | (2) | 270 | 0.2 | 2,600 |
| 3 | (3) | 200 | 0.3 | 3,000 |
| 4 | (4) | 155 | 0.85 | 1,550 |
| 5 | (5) | 230 | 0.2 | 3,000 |
| 6 | (12) | 145 | 0.3 | 1,600 |

As the results show, the novel electrophotographic recording materials possess high photoconductivity and low conductivity in the dark. Thus, for example, the layer of Example 1 exhibits a decrease in potential from 600 to 599.8 volts in the course of about 0.2 second in the dark, while the same layer, when exposed with a high-pressure xenon lamp having a luminous intensity of 0.85 mw.cm$^{-2}$ for same time, exhibits a decrease in potential from 600 to 300 volts. The recording material can be charged to a maximum of more than 1,500 volts, which is substantially above the surface potential required in copying machines (about 700 volts), and is hence very useful for the copying sector.

EXAMPLE 7

The procedure described in Examples 1 to 6 was followed, except that the charge-transporting layer was prepared from 55 parts of a copolymer of 80% of styrene with 20% of maleic anhydride, and 45 parts of 2-(4'-ethylbenzylaminophenyl)-1,2,3-benzotriazole. Xerographic measurements on the recording material showed that the potential decreased by 15% in the course of 20 seconds in the dark, while exposure of the layer to white light from a high-pressure xenon lamp of 0.85 mw.cm$^{-2}$ luminous intensity caused the potential to decrease to half its value in 0.22 second. When this layer was used as a copying film in a conventional copying machine employing a dry toner, a large number of copies of good quality were obtained.

EXAMPLES 8 TO 22

55 parts of a copolymer containing 70% of styrene, 6% of maleic anhydride and 24% of acrylic acid and having a mean molecular weight of about 2,000, 45 parts of one of the benzotriazoles listed above under (1) to (15), and 0.3 part of methyl violet (C.I. 42535) were dissolved in ethyl acetate, the solution was applied to an electrolytically roughened and subsequently anodized aluminum sheet of 0.15 mm thickness, which constituted the electrically conductive base, the solvent was evaporated off in the air and drying was carried out for 30 minutes at 85° C., the resulting dry layer being 4 μm thick. The xerographic measurements are shown in Table 2.

TABLE 2

Xerographic measurements on the recording materials of Examples 8 to 22.

| Example | Benzo-triazole | A (ms) | C (V) | D (%) | E (%) | F (V/s) | G (V) |
|---|---|---|---|---|---|---|---|
| 8 | (1) | 190 | 600 | 14 | 93 | 2,540 | 480 |
| 9 | (2) | 215 | 520 | 25 | 95 | 2,000 | 370 |
| 10 | (3) | 185 | 540 | 16 | 91 | 2,420 | 410 |
| 11 | (4) | 210 | 580 | 17 | 91 | 2,120 | 440 |
| 12 | (5) | 190 | 600 | 19 | 96 | 2,360 | 470 |
| 13 | (6) | 270 | 670 | 31 | 82 | 1,870 | 460 |
| 14 | (7) | 160 | 660 | 18 | 95 | 2,960 | 540 |
| 15 | (8) | 240 | 680 | 33 | 81 | 1,800 | 460 |
| 16 | (9) | 260 | 510 | 25 | 78 | 1,825 | 380 |
| 17 | (10) | 190 | 770 | 31 | 88 | 1,980 | 530 |
| 18 | (11) | 210 | 540 | 25 | 82 | 1,800 | 410 |
| 19 | (12) | 160 | 570 | 19 | 95 | 2,700 | 460 |
| 20 | (13) | 170 | 680 | 16 | 91 | 2,750 | 570 |
| 21 | (14) | 190 | 660 | 25 | 89 | 2,580 | 500 |
| 22 | (15) | 240 | 580 | 20 | 86 | 1,875 | 470 |

EXAMPLE 23

50 parts of a copolymer containing 60% of styrene and 40% of monomethyl maleate and having a mean molecular weight $\overline{M}_w$ of 10,000, 50 parts of 2-(4'-diethylaminophenyl)-1,2,3-benzotriazole and 0.2 part of crystal violet (C.I. 42555) were applied, from a 5% strength solution in tetrahydrofuran, to an electrolytically roughened and anodized aluminum foil of 0.15 mm thickness to give a layer which was about 4 μm thick when dry.

This printing plate was charged by means of a high-voltage corona and then exposed imagewise in a camera for 25 seconds. The plate was then developed with a powder toner, which was baked at 160° C. to give an abrasion-resistant surface. The non-toned area of the layer was washed off with a mixture of 0.5% of sodium carbonate, 25% of isopropanol and 74.5% of water, the aluminum surface being bared by this procedure. The solutions were applied to the layer by rubbing with a wad of cottonwool. The differentiation between hydrophilic and oleophilic areas, which is desirable in offset printing, was obtained, the surface of the base constituting the hydrophilic areas.

After treatment with the alkaline liquid, the printing plate was washed with water, and the hydrophilic character of the base surface was further increased by wiping it with dilute phosphoric acid solution. The plate was inked with a fatty ink and then used for printing in a conventional manner in an offset printing press.

We claim:

1. An electrophotographic recording material comprising an electrically conductive base, charge carrier-producing compounds and charge carrier-transporting compounds, which contains an effective amount, as charge carrier-transporting compounds, of one or more compounds of the formula (I)

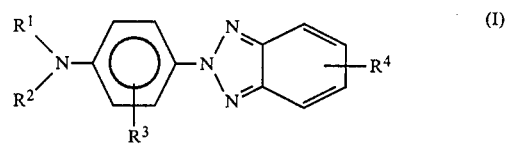

where $R^1$ and $R^2$ are identical or different and are each hydrogen, alkyl, allyl, benzyl or unsubstituted or substituted phenyl, or $R^1$ and $R^2$ together are

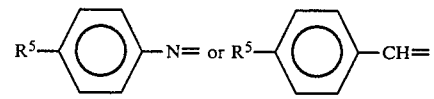

where $R^5$ is $NR^1R^2$, $R^3$ is hydrogen, alkyl, alkoxy or halogen and $R^4$ is hydrogen, alkyl, alkoxy, vinyl, allyl, dialkylamino, nitro, cyano or acryloyl.

2. An electrophotographic recording material as described in claim 1, wherein, in formula (I), $R^1$ is hydrogen, alkyl, benzyl or phenyl, $R^2$ is alkyl, benzyl or phenyl, $R^3$ is hydrogen and $R^4$ is hydrogen, alkoxy or halogen.

3. An electrophotographic recording material as described in claim 1, which comprises an electrically conductive base, a layer containing charge carrier-producing compounds and another layer containing charge carrier-transporting compounds of the formula (I) given in claim 1.

4. A recording material for the production of an electrophotographic printing plate as described in claim 1, which comprises, on a 0.08–0.6 mm thick base suitable for printing plates, a photosemiconducting layer containing
  (a) one or more binders,
  (b) one or more charge carrier-transporting compounds as described in claim 1 and
  (c) one or more dyes as sensitizers, with or without
  (d) further additives.

5. A recording material as described in claim 4, wherein the binder is soluble in basic aqueous or alcoholic solvents.

6. A recording material as described in claim 5, wherein the binder has a mean molecular weight of from 800 to 50,000.

7. A recording material as described in claim 4, wherein the binder is a styrene/maleic anhydride/acrylic or methacrylic acid copolymer containing from 5 to 50% by weight of maleic anhydride as copolymerized units, and from 5 to 35% by weight of acrylic and/or methacrylic acid as copolymerized units.

8. A recording material for the production of an electrophotographic printing plate as described in claim 2, which comprises, on a 0.08–0.6 mm thick base suitable for printing plates, a photosemiconducting layer containing
(a) one or more binders,
(b) one or more charge carrier-transporting compounds as described in claim 2, and
(c) one or more dyes as sensitizers, with or without
(d) further additives.

9. An electrophotographic recording material as described in claim 1, wherein the alkyl groups of the compounds of formula I have from 1 to 2 carbon atoms and wherein the alkoxy groups of the compounds of formula I have 1 or 2 carbon atoms.

10. An electrophotographic recording material as described in claim 2, wherein the alkyl groups of the compounds of formula 1 have from 1 to 2 carbon atoms.

11. A recording material as described in claim 4, wherein the printing plate is an offset printing plate.

12. A recording material as defined in claim 1, wherein the components of a single-layer system are present in the following amounts:
(a) from 45 to 75 parts by weight of a binder;
(b) from 30 to 60 parts by weight of charge carrier-transport compounds of the formula I; and
(c) from 0.05 to 0.8 parts by weight of a charge-carrier-producing compound.

13. A recording material as defined in claim 12, which further includes from 5 to 25 parts by weight of another, essentially inactive binder.

14. A recording material as defined in claim 3, wherein the charge-transporting layer (b) contains (b1) from 30 to 60 parts by weight of one or more charge carrier-transporting compounds (I) and (b2) from 45 to 75 parts by weight of an organic binder.

* * * * *